(12) United States Patent
Parkinson

(10) Patent No.: US 9,084,903 B2
(45) Date of Patent: Jul. 21, 2015

(54) COMPOSITIONS COMPRISING ALGINATES WITH HIGH GULURONIC ACID/MANNURONIC ACID RATIO FOR USE IN THE TREATMENT OF DENTINE HYPERSENSITIVITY

(75) Inventor: Charles Richard Parkinson, Weybridge (GB)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/515,415

(22) PCT Filed: Dec. 15, 2010

(86) PCT No.: PCT/EP2010/069699
§ 371 (c)(1),
(2), (4) Date: Jun. 12, 2012

(87) PCT Pub. No.: WO2011/073299
PCT Pub. Date: Jun. 23, 2011

(65) Prior Publication Data
US 2012/0251468 A1 Oct. 4, 2012

(30) Foreign Application Priority Data

Dec. 17, 2009 (GB) .................................. 0922133.4

(51) Int. Cl.
*A61K 31/734* (2006.01)
*A61Q 11/00* (2006.01)
*A61K 8/73* (2006.01)

(52) U.S. Cl.
CPC ............... *A61Q 11/00* (2013.01); *A61K 8/733* (2013.01); *A61K 31/734* (2013.01)

(58) Field of Classification Search
CPC ... A61K 2300/00; A61K 45/06; A61K 8/733; A61K 31/734; A61Q 11/00

USPC .................. 424/49, 488, 493; 514/779; 536/3
See application file for complete search history.

(56) References Cited

U.S. PATENT DOCUMENTS

| 5,192,362 A | * | 3/1993 | Harvey et al. ................... 106/35 |
| 5,885,551 A | * | 3/1999 | Smetana et al. ................ 424/49 |
| 2007/0082027 A1 | * | 4/2007 | Aimutis et al. ............... 424/439 |

FOREIGN PATENT DOCUMENTS

| JP | 2006 206581 | | 8/2006 |
| JP | 2006/206581 A | * | 8/2006 |
| JP | 2008 007413 | | 1/2008 |
| WO | WO 98/02488 A1 | | 1/1998 |
| WO | WO 98/12228 A1 | | 3/1998 |
| WO | WO 2007/066837 | | 6/2007 |
| WO | WO 2007066837 A1 | * | 6/2007 |

OTHER PUBLICATIONS

Walters, Patricia. Dentinal Hypersensitivity. May 15, 2005. The Journal of Contemporary Dental Practice. pp. 1-10.*
Database WPI; Week 200809, Thomson Scientific, London, GB; AN 2008-B35366, XP002620330, & JP 2008 007413 A (Lion Corp) Jan. 17, 2008 *abstract.
Database WPI; Week 200659, Thomson Scientific, London, GB; AN 2006-572575 XP002620331, & JP 2006 206581 A (Lion Corp) Aug. 10, 2006.
Pashley D. H. et al.: "The effects of outward forced convective flow on inward diffusion in human dentine in vitro" Archives of Oral Biology, Pergamon Press, Oxford, GB vol. 38, No. 7, Jul. 1, 1993 pp. 577-582, XP022865224, ISSN: 0003-9969, DOI: 10.1016/0003-9969(93)90122-3.

* cited by examiner

*Primary Examiner* — Frederick Krass
*Assistant Examiner* — Tracy Liu
(74) *Attorney, Agent, or Firm* — Nora L. Stein; Theodore R. Furman

(57) ABSTRACT

The present invention relates to oral care compositions comprising certain alginates for the treatment of dentine hypersensitivity and to their use.

3 Claims, 1 Drawing Sheet

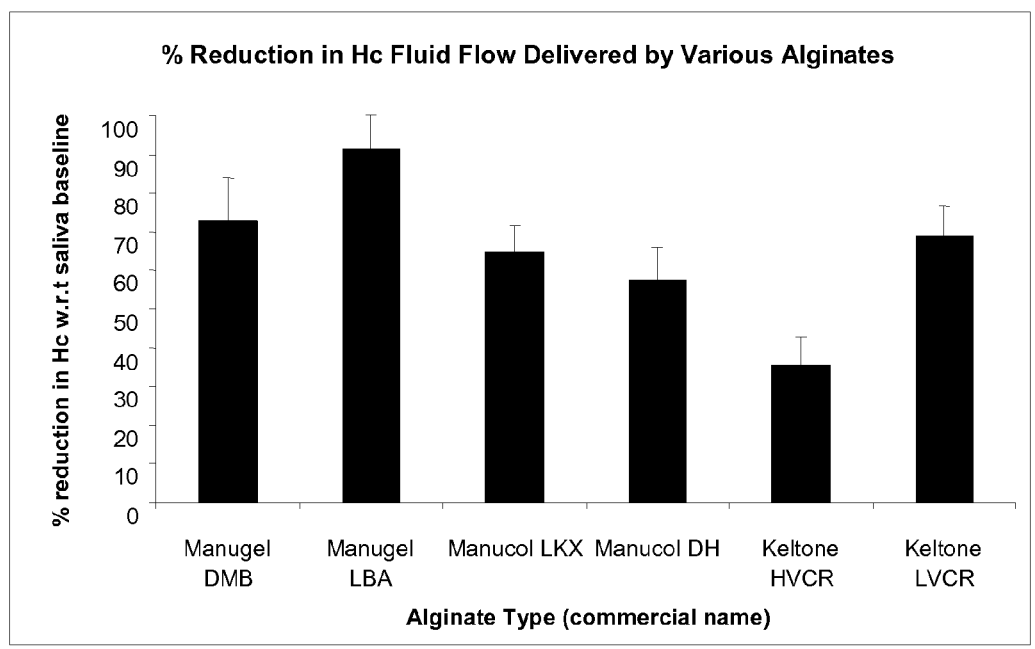

COMPOSITIONS COMPRISING ALGINATES WITH HIGH GULURONIC ACID/MANNURONIC ACID RATIO FOR USE IN THE TREATMENT OF DENTINE HYPERSENSITIVITY

This application is a 371 national phase entry of International Application No. PCT/EP2010/069699, filed Dec. 15, 2010, which claims the priority of GB Application No. GB 0922133.4 filed Dec. 17, 2009, which are incorporated herein in their entirety.

FIELD OF THE INVENTION

The present invention relates to oral care compositions comprising certain alginates for the treatment of dentine hypersensitivity and to their use.

BACKGROUND OF THE INVENTION

Dentine hypersensitivity is a relatively common condition thought to affect up to 35% of the population. The condition, which has been described as 'pain arising from exposed dentine typically in response to chemical, thermal, tactile or osmotic stimuli, which cannot be explained as arising from any other form of dental defect or pathology' is believed to result from the exposure of underlying dentine to the oral environment ((Addy M, Mostafa P, Absi E G, and Adams, D. Cervical dentine hypersensitivity: Aetiology and management with particular reference to dentifrices. In: Proceedings of Symposium on Hypersensitive Dentine. Origin and Management (ed. N. H. Rowe), pp 147. E. & S Livingstone Ltd., Edinburgh and London. 1985).

Dentine is a permeable mineralised tissue that forms the bulk of the tooth and is perforated by numerous tubules that extend from the pulp to the enamel-dentine or cementum-dentine junction. When enamel erodes or gums recede, the tubules become exposed, providing pathways between the oral cavity and nerve fibres in the pulp. It is a common observation that hypersensitive dentine is devoid of a smear layer, and it has been suggested that in hypersensitive teeth the dentine tubules are open at the tooth surface and patent to the pulp.

One theory on dentine hypersensitivity, called the hydrodynamic theory (Brännström, M., and Astrom, A., A Study on the Mechanism of Pain Elicit from Dentin. *Journal of Dental Research*, 1964, 43, 619), suggests that the exposure of the tubules to external stimuli can cause irritation of the nerve and lead to discomfort. A consequence of the hydrodynamic theory is that it implies that dentine hypersensitivity may be treated by making the nerve in the tooth less sensitive or by occluding the tubules to limit exposure of the nerve to external stimuli.

Tubule occluding agents, such as oxalate salts and strontium salts serve to seal or block the dentine tubules and act to diminish the effect of external stimuli. Such occluding agents may also work synergistically with nerve desensitising agents, such as potassium salts, to help reduce the natural flushing of the nerve desensitising agent from the tubule. In diffusion studies, tubule occluding compounds have been shown to increase the retention of nerve desensitising agents through dentine disks against the physiologically relevant outward fluid flow, (Pashley D H, Mathews W G, The effects of outward forced convective flow on inward diffusion in human dentine in vitro, *Arch Oral Biol*, 1993 41, 7, 679-687).

These studies suggest that under in vivo conditions the occlusion of dentine tubules may inhibit outward fluid flow without inhibiting the inward diffusion of soluble nerve depolarising compounds.

Many agents have been proposed for treating dentine hypersensitivity, for instance formaldehyde, sodium or stannous fluoride, zinc chloride, silver nitrate, sodium citrate/citric acid (U.S. Pat. No. 4,011,309, Marion Laboratories Inc), strontium salts (U.S. Pat. No. 3,122,483, Rosenthal M. W., to Block drug company), potassium and other alkali metal nitrates (UK1 466 930 Hodosh, M).

U.S. Pat. No. 4,775,525 (Pera), relates to formulations and methods comprising sodium alginate for promoting oral hygiene in particular for reducing tooth decay by removing dental plaque.

U.S. Pat. No. 5,885,551 (Smetana et al), relates to a method of treating dentine hypersensitivity by administering a therapeutic amount of an alginate to a hypersensitive tooth.

It has now been surprisingly found that certain alginates as described herein exhibit enhanced dentine tubule occluding properties relative to other alginates, such as those described in U.S. Pat. No. 5,885,551. Accordingly alginates of use in the present invention are expected to provide improved treatments for dentine hypersensitivity.

DETAILED DESCRIPTION OF THE INVENTION

Brief Description of the Drawings

FIG. 1 is a graphic depiction of the initial percentage reduction in dentine permeability in the Hydraulic Conductance model.

Alginates are salts of alginic acid and have been described as comprising a mixture of polyuronic acids $[(C_6H_8O_6)_n]$ composed of residues of $\alpha$-L-glucoronic acid and $\beta$-D-mannuronic acid. An alginate can be a high guluronic acid alginate or a high mannuronic acid alginate. Alginates described in U.S. Pat. No. 5,885,551 are sodium alginates commercially available as Keltone LVCR® and Keltone HVCR®, and are each high mannuronic acid alginates i.e. they exhibit a ratio of $\alpha$-L-guluronic to $\beta$-D mannuronic acid of less than about 1:1, of about 0.6:1 to about 0.7:1.

According to the present invention there is provided an oral care composition comprising an alginate having a ratio of $\alpha$-L-guluronic acid to $\beta$-D-mannuronic acid higher than 1.0:1.0. for use in treating dentine hypersensitivity.

An alginate for use in the present invention exhibits a higher than 1.0:1.0 ratio of $\alpha$-L-guluronic acid to $\beta$-D-mannuronic acid (hereinafter referred to as a G:M ratio) such as in the range from about 1.2:1.0 to about 1.8:1.0 e.g. about 1.3:1.0, about 1.4:1.0, about 1.5:1.0, about 1.6:1.0, or about 1.7:1.0. Examples of high guluronic alginates having higher than 1.0:1.0 G:M ratios include those that are commercially available as Manugel LBA, Manugel GHB and Manugel DBP, manufactured by ISP (International Speciality Products, Waterfield, Tadworth Surrey. UK), which each has a G:M ratio of about 1.5:1.0. In one embodiment the alginate is Manugel LBA. Most suitably an alginate for use in the invention comprises a ratio of $\alpha$-L-guluronic acid to $\beta$-D-mannuronic acid of about 1.5:1.0.

An alginate for use in the invention can exhibit any number average molecular weight range (e.g. from about $1 \times 10^2$ Daltons to about $1 \times 10^6$ Daltons) such as a high molecular weight range (about $2.05 \times 10^5$ to about $3 \times 10^5$ Daltons) e.g. Manugel DPB; a medium molecular weight range (about $1.38 \times 10^5$ to about $2 \times 10^5$ Daltons) e.g. Manugel GHB; or a low molecular weight range (about $2 \times 10^4$ to about $1.35 \times 10^5$ Daltons) e.g.

Manugel LBA. In one embodiment the alginate comprises an average molecular weight range from about $2\times10^4$ to about $1.35\times10^5$ Daltons. Molecular weight can be determined by a number of methods known in the art for example size exclusion chromatography with multi-laser light scattering.

An alginate for use in a composition according to the invention comprises a viscosity in the range from about 1 to about 500 centipoise (cP) when measured as a 1% w/w solution in water at 37° C., on a Brookfield viscometer (Brookfield Engineering Laboratories, Inc., 11 Commerce Boulevard, Middlesboro, Mass. USA). More suitably an alginate for use in the invention has a low viscosity, suitably in the range from about 1 to about 100 cP, more suitably in the range from about 1 to about 50 cP, such as from about 1 to about 20 cP, when measured as 1% w/w solution in water at 37° C., on a Brookfield viscometer. In particular, an alginate comprising a high ratio of α-L-guluronic acid to β-D-mannuronic acid guluronic ratio (greater than 1.0:1.0) and a low viscosity as herein described i.e. in the range from about 1 to about 100 cP, for example Manugel LBA, has been found to demonstrate increased levels of tubule occlusion, relative to other alginates not comprising these features.

A composition of the present invention suitably comprises from about 0.5 to about 6.0% wt of an alginate, for example from about 1.0% to about 3.0% wt. of an alginate.

Compositions of the present invention will contain appropriate formulating agents such as abrasives, surfactants, thickening agents, humectants, flavouring agents, sweetening agents, opacifying or colouring agents, preservatives and water, selected from those conventionally used in the oral care composition art for such purposes. Examples of such agents are as described in EP 929287.

Suitable surfactants for use in the invention include polyethylene glycols (PEG), hydrogenated caster oils, sorbitan esters, polyethylene-polypropylene tri-block copolymers (such as Poloxamers™). Preferred surfactants include PEG-40 or PEG-60 hydrogenated castor oil and sorbitan esters.

Suitable humectants for use in compositions of the invention include glycerine, sorbitol, xylitol, propylene glycol or polyethylene glycol, or mixtures thereof; which humectant may be present in the range from 5 to 70%.

Suitable flavouring agents for use in the present invention include peppermint, spearmint, and fruit flavours. If desired, additional salivary stimulants can be included such as edible organic acids, e.g. citric acid.

Suitable preservatives for use in the invention include parabens (methyl and propyl parabens), sodium benzoate, and potassium sorbate.

Compositions of the present invention may further comprise a source of fluoride ions such as those provided by sodium fluoride, sodium monofluorophosphate, tin (II) fluoride or an amine fluoride in an amount to provide from 25 to 3500 ppm fluoride, preferably from 100 to 1500 ppm.

Additional ingredients suitable for use in the invention include remineralising agents, antimicrobial agents, anti-caries agents, anticalculus agents, moisturising agents, breath freshening agents and desensitising agents.

Suitable antimicrobial agents for use in the invention include chlorhexidine, cetylpyridinium chloride, zinc salts or triclosan. Preferred antimicrobial agents are cetylpyridinium chloride, chlorhexidine and zinc salts.

Examples of desensitising agents include tubule blocking agents or nerve desensitising agents and mixtures thereof, for example as described in WO 02/15809. Suitable desensitising agents include a strontium salt such as strontium chloride, strontium acetate or strontium nitrate or a potassium salt such as potassium citrate, potassium chloride, potassium bicarbonate, potassium gluconate and especially potassium nitrate.

The oral care compositions of the present invention are typically formulated in the form of toothpastes, sprays, mouthwashes, gels, lozenges, chewing gums, tablets, pastilles, and instant powders. In one embodiment a composition of the invention is in the form of a mouthwash or a dentifrice. In one embodiment a composition of the invention is a mouthwash.

Mouthwash and mouth spray compositions may be provided in a "ready to use" form; as a concentrated solution, for dilution by the user immediately prior to use; or in solid form, such as a tablet or as instant powder in a sachet, for dissolution by the user immediately prior to use. Tablets may suitably be prepared using xylitol and/or sorbitol as the major ingredient. The sachets and tablets may be formulated to provide, on dissolution, a still mouthwash, or, by the incorporation of a suitable effervescent couple, for instance sodium carbonate/bicarbonate and citric acid, an effervescent mouthwash.

A composition according to the present invention may be prepared by admixing the ingredients in the appropriate relative amount in any order that is convenient and if necessary, adjustment of the pH to the desired value.

The compositions according to the present invention will have a pH which is orally acceptable, typically ranging from about pH 5 to 10 and more preferable pH 5.5 to 8.

In a further aspect of the present invention there is provided an oral care composition for use in the treatment of dentine hypersensitivity comprising an alginate as hereinbefore described.

In a further aspect of the present invention there is provided a method for the treatment of dentine hypersensitivity which comprises applying an effective amount of a composition comprising an alginate as herein before described to an individual in need thereof.

The invention is further illustrated by the following Examples.

Example 1

Hydraulic Conductance (HC) Measurement

The He model is based on the original design by Pashley et al (Greenhill J D, Pashley D H. The effects of desensitising agents on the hydraulic conductance of human dentin in vitro. *J. Dent Res* 1981; 60:686-698). Etched dentine disks are prepared from human molars and placed pulpal side down in a split chamber device. The bottom portion of the chamber is closed except for a single inlet port connected to a fluid reservoir, containing simulated dentine fluid, and the top portion of the chamber is open to air. Hydrostatic pressure is applied to the dentine disk via the bottom inlet port by increasing the pressure inside the pressure vessel containing the simulated dentine fluid to 1 p.s.i. After a stabilisation period the flow rate of fluid passing through the dentine disk is measured.

Protocol

Dentine permeability as a function of hydraulic conductance was measured for each specimen at baseline and after treatment with each agent (3% w/w alginate dispersed in water). Each disk served as its own control. Prior to treatment the hydraulic conductance of each specimen was measured following application of a salivary pellicle. This value was set to represent 100% permeability, and is termed the baseline permeability of the disk. After application of the sealant the hydraulic conductance was assessed (over 5 minutes). This value was used to calculate the percentage of permeability reduction for the particular sealant. Following treatment the disks were subjected to simulated oral challenges. In order, these consisted of (i) a 5 sec. rinse with 10% citric acid, (ii) a 30 sec. brush while rinsed with 0.17% KCl, and (iii) the application of a 10 sec. purge pressure (12 p.s.i on the pulpal side of the disk). Three dentine disks were used in each treatment group.

Results

The results obtained from the He experiment are detailed in Table 1. The initial percentage reduction in dentine permeability in the He model is shown graphically in FIG. 1. Achieving an 80% or more reduction in dentine permeability (hydraulic conductance) is considered desirable (described as 'good') tubule occluding systems.

TABLE 1

Percentage Reduction in Hydraulic Conductance Measured Relative to Baseline for a Variety of Alginates (SD in parentheses).

| Type of Alginate (brand name). | Initial % reduction in Hc w.r.t baseline flow. | % Reduction in Hc after 20 Hrs & following an additional treatment | % Reduction in Hc after 40 Hrs & following an additional treatment | % reduction in Hc on application of a purge challenge (10 p.s.i). |
|---|---|---|---|---|
| Manugel DMB | 73.0 (11.1) | 95.9 (5.8) | 99.0 (6.6) | 78.0 (8.3) |
| Manugel LBA | 91.0 (8.9) | 93.1 (7.9) | 96.1 (4.3) | 80.4 (8.5) |
| Manucol DH* | 57.8 (8.4) | 97.8 (10.0) | 99.0 (5.5) | 97.6 (10.5) |
| Manucol LKX* | 64.9 (6.6) | 93.2 (10.5) | 96.2 (9.9) | 78.0 (11.2) |
| Keltone HVCR* | 35.7 (6.9) | 78.6 (9.6) | 99.0 (6.9) | 71.0 (11.0) |
| Keltone* LVCR | 69.1 (7.7) | 92.4 (4.3) | 94.8 (7.2) | 70.2 (4.3) |

Alginates designated with an * comprise a low G:M ratio (i.e. less than 1.0:1.0) and are outside the scope of the present invention but are included herein for comparative purposes.

The G:M ratios of the alginates tested are provided below

| Alginate (Trade name) | G:M Ratio (High/Med/Low) |
|---|---|
| Manugel DMB | High (>1.5:1.0) |
| Manugel LBA | High (>1.5:1.0) |
| Manucol DH | Low (<1.0:1.0) |
| Manucol LKX | Low (<1.0:1.0) |
| Keltone HVCR | Low (<1.0:1.0) |
| Keltone LVCR | Low (<1.0:1.0) |

Example 2

Typical Dentifrice Composition

| Ingredient | w/w % |
|---|---|
| Titanium Dioxide | 1 |
| Flavour | 1.1 |
| Sodium saccharin | 0.3 |
| Sodium fluoride | 0.315 |
| Sorbitol | 30 |
| Alginate | 3 |
| Glycerin | 14 |
| Abrasive system | 7 |
| Thickener | 8 |
| Surfactant | 1 |
| Purified water | 34.285 |

Example 3

Typical Mouthwash Composition

| Ingredient | % w/w |
|---|---|
| Purified water | 84 |
| Glycerin | 7.6 |
| Sorbitol | 5 |
| Alginate | 1.5 |
| Surfactant | 1 |
| Sodium benzoate | 0.5 |
| Flavour | 0.15 |
| Cetylpyridinium chloride | 0.05 |
| Methyl paraben | 0.1 |
| Sodium fluoride | 0.05 |
| Sodium saccharin | 0.05 |
| Total | 100.00000 |

The invention claimed is:

1. A method for treating dentine hypersensitivity which comprises applying an effective amount of an oral care composition comprising as an active agent an alginate which is Manugel LBA having a ratio of α-L-guluronic acid to β-D-mannuronic of greater than 1.5:1.0 and a molecular weight range of from about $2 \times 10^4$ to about $1.35 \times 10^5$ Daltons and a viscosity in the range 1 to 100 cP when measured as a 1% w/w solution in water at 37° C., to an individual in need thereof.

2. The method as claimed in claim 1, wherein the alginate is present in an amount from about 0.5% wt. to about 6% wt. of the composition.

3. The method as claimed in claim 1, wherein the composition is in the form of a mouthwash.

* * * * *